US012678121B2

(12) United States Patent
Saito et al.

(10) Patent No.: US 12,678,121 B2
(45) Date of Patent: Jul. 14, 2026

(54) RADIATION IMAGING SYSTEM, METHOD OF OPERATING RADIATION IMAGING SYSTEM, AND COMPUTER READABLE STORAGE MEDIUM

(71) Applicant: CANON KABUSHIKI KAISHA, Tokyo (JP)

(72) Inventors: Yohei Saito, Kanagawa (JP); Yutaka Ishinari, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 176 days.

(21) Appl. No.: 18/670,337

(22) Filed: May 21, 2024

(65) Prior Publication Data

US 2024/0389967 A1 Nov. 28, 2024

(30) Foreign Application Priority Data

May 23, 2023 (JP) ................................. 2023-084385

(51) Int. Cl.
*A61B 6/00* (2024.01)

(52) U.S. Cl.
CPC .............. *A61B 6/566* (2013.01); *A61B 6/542* (2013.01); *A61B 6/545* (2013.01); *A61B 6/548* (2013.01)

(58) Field of Classification Search
CPC ......... A61B 6/566; A61B 6/542; A61B 6/545; A61B 6/548; A61B 6/56
See application file for complete search history.

(56) References Cited

U.S. PATENT DOCUMENTS

| | | | | | |
|---|---|---|---|---|---|
| 2002/0080918 A1* | 6/2002 | Sako | ...................... | A61B 6/548 |
| | | | | | 378/115 |
| 2016/0025865 A1* | 1/2016 | Wayama | ................ | A61B 6/542 |
| | | | | | 250/370.07 |

FOREIGN PATENT DOCUMENTS

| | | | | | |
|---|---|---|---|---|---|
| JP | 2012135524 A | * | 7/2012 | ............. | A61B 6/548 |
| JP | 5914503 B2 | | 5/2016 | | |
| JP | 2018042782 A | * | 3/2018 | ............. | G01N 23/04 |

* cited by examiner

*Primary Examiner* — Kiho Kim
(74) *Attorney, Agent, or Firm* — Canon U.S.A., Inc. IP Division

(57) ABSTRACT

A radiation imaging system comprising a control apparatus that controls a radiation generating apparatus which exposes a radiation and a radiation imaging apparatus that detects the exposed radiation and generates a radiation image, wherein the radiation imaging apparatus has a first communication mode in which a signal related to a stop of exposure of the radiation is wirelessly transmitted and a second communication mode in which at least one signal not related to the stop of exposure of the radiation is wirelessly transmitted, and wherein communication in the first communication mode includes communication at power lower than communication in the second communication mode.

14 Claims, 9 Drawing Sheets

START

S501 — TRANSMIT IMAGING INFORMATION IN SECOND COMMUNICATION MODE (AT HIGH OUTPUT)

S502 — START EXPOSURE

S503 — DETECTED DOSE ≥ THRESHOLD VALUE?

NO

YES

S504 — TRANSMIT EXPOSURE STOP SIGNAL IN FIRST COMMUNICATION MODE (AT LOW OUTPUT)

S505 — TRANSMIT IMAGE IN SECOND COMMUNICATION MODE

END

FIG. 6

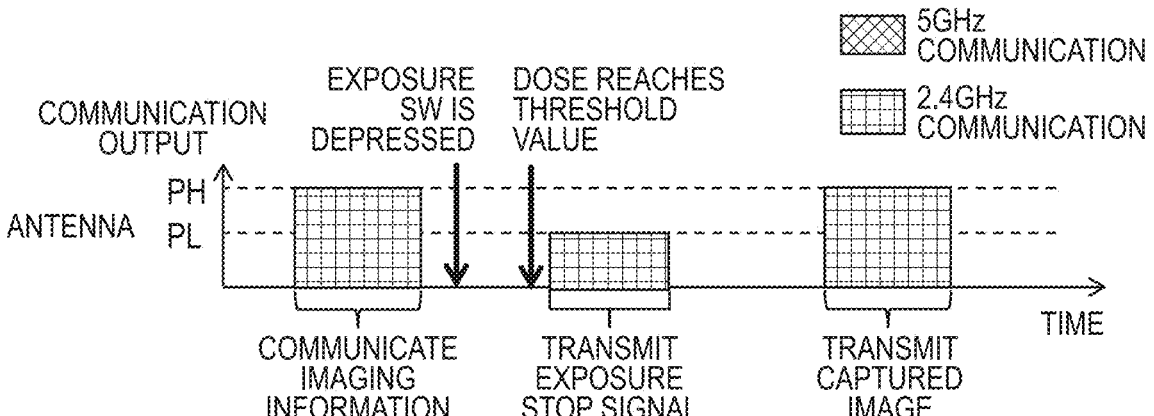

5GHz COMMUNICATION 2.4GHz COMMUNICATION

COMMUNICATION OUTPUT

EXPOSURE SW IS DEPRESSED

DOSE REACHES THRESHOLD VALUE

ANTENNA   PH

PL

TIME

COMMUNICATE IMAGING INFORMATION

TRANSMIT EXPOSURE STOP SIGNAL

TRANSMIT CAPTURED IMAGE

Figure 10:
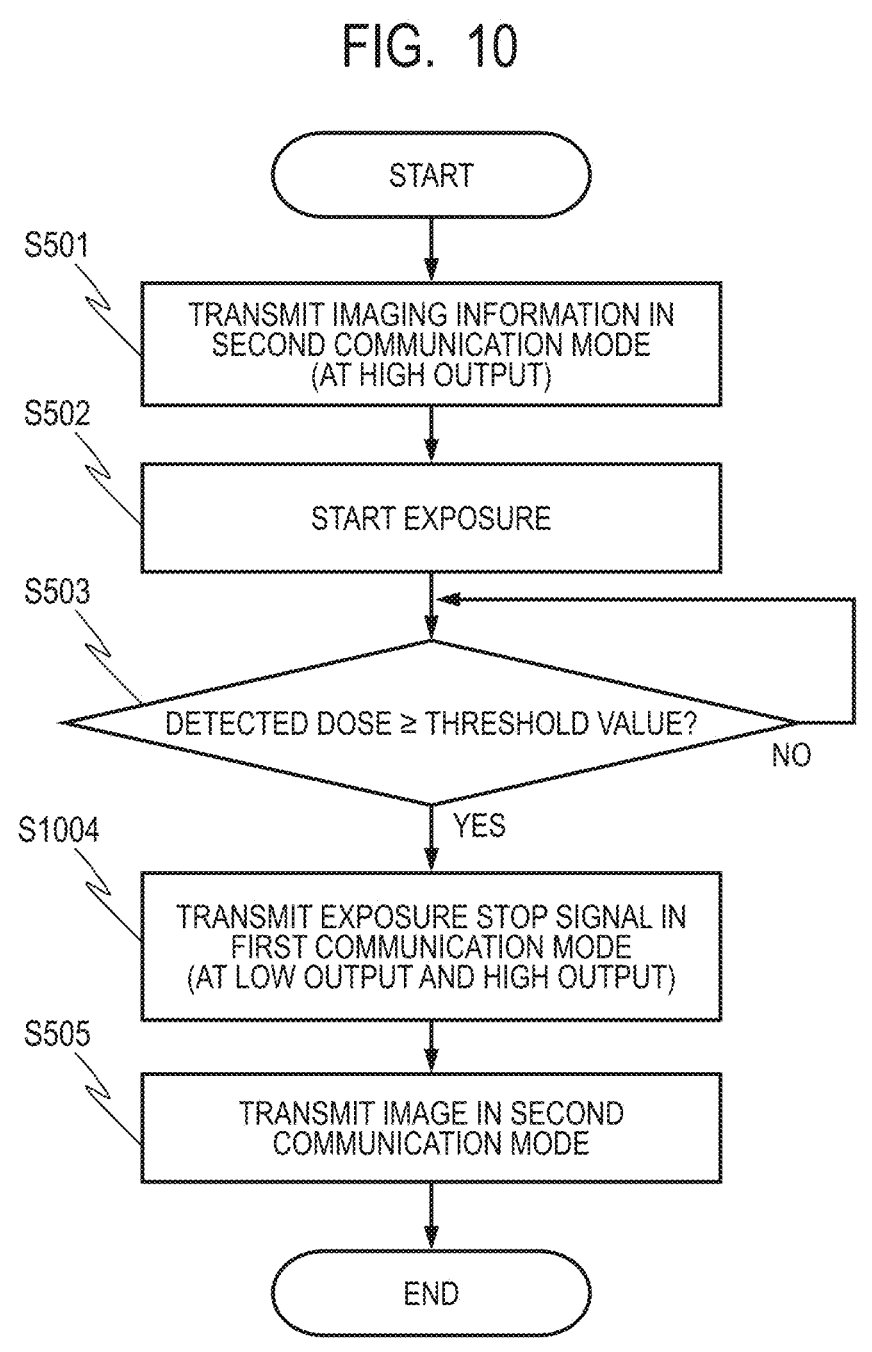

START

S501

TRANSMIT IMAGING INFORMATION IN
SECOND COMMUNICATION MODE
(AT HIGH OUTPUT)

S502

START EXPOSURE

S503

DETECTED DOSE ≥ THRESHOLD VALUE?

NO

YES

S1004

TRANSMIT EXPOSURE STOP SIGNAL IN
FIRST COMMUNICATION MODE
(AT LOW OUTPUT AND HIGH OUTPUT)

S505

TRANSMIT IMAGE IN SECOND
COMMUNICATION MODE

END

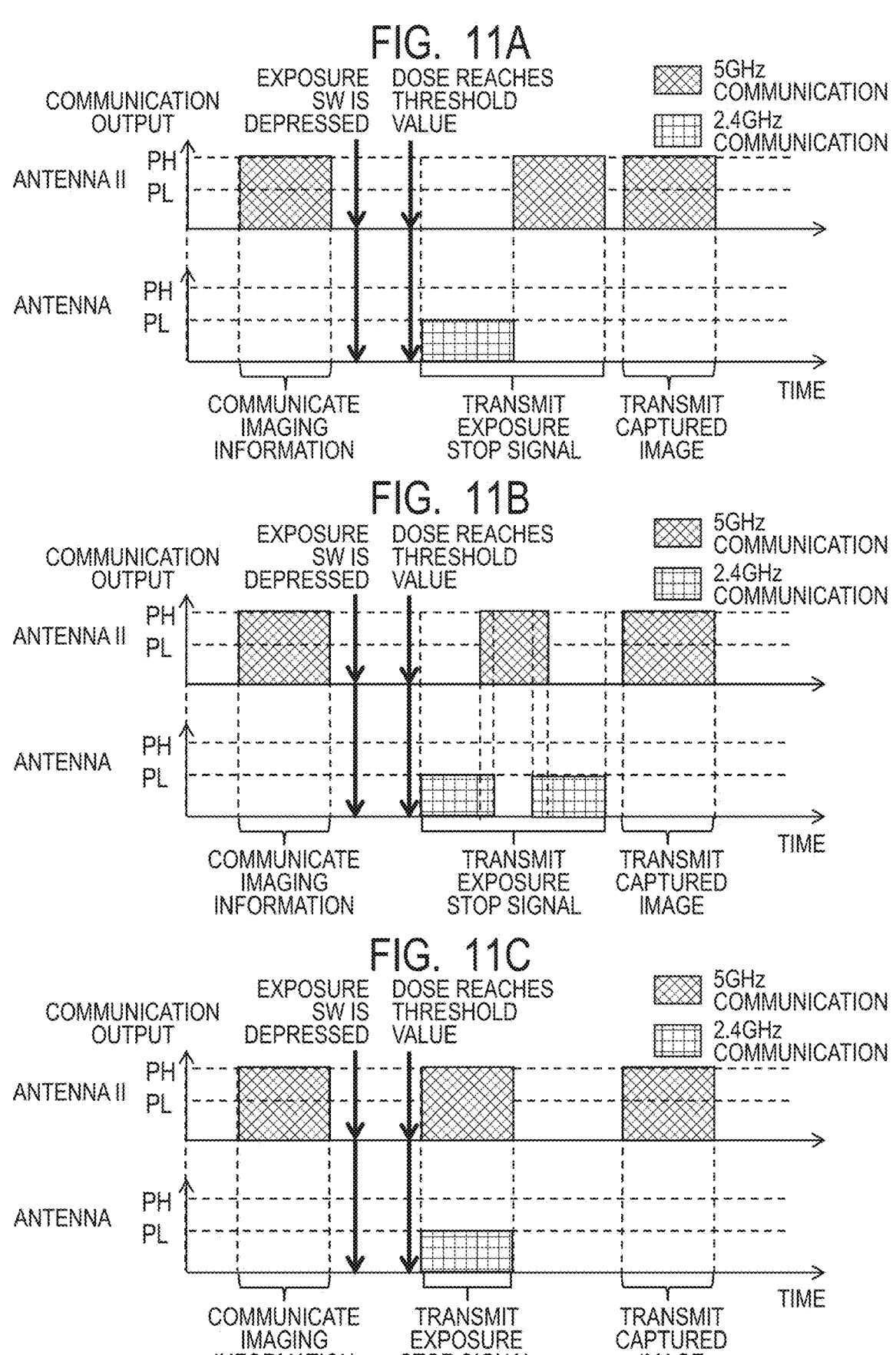

RADIATION IMAGING SYSTEM, METHOD OF OPERATING RADIATION IMAGING SYSTEM, AND COMPUTER READABLE STORAGE MEDIUM

BACKGROUND OF THE DISCLOSURE

Field of the Disclosure

The present disclosure relates to a radiation imaging system, a method of the radiation imaging system, and a computer readable storage medium.

Description of the Related Art

An X-ray imaging system that irradiates object to be examined with X-rays and images an intensity distribution of the transmitted X-rays is widely used in the medical field. In recent years, an X-ray imaging system is sometimes used in combination with a portable X-ray sensor that includes a sensor unit for converting X-rays into an image signal, which is driven with a battery, and wirelessly communicates an image signal. Further, an X-ray imaging system having an auto exposure control (AEC) function in which the X-ray dose is measured during irradiation and the X-ray irradiation is stopped if the X-ray dose reaches a predetermined value is also known. In addition, a portable X-ray sensor having an AEC function in which wireless communication is performed and the X-ray irradiation is stopped if the X-ray dose reaches a predetermined value, which is obtained by combining the above-mentioned technique, is also known.

In a case of realizing the AEC function using wireless communication, if an X-ray exposure stop signal is delayed, the X-ray exposure cannot be stopped at the desired X-ray dose, and the desired image cannot be obtained, resulting in invalid exposure. In this regard, Japanese Patent No. 05914503 discloses a technique for reducing the delay by communicating the AEC signal related to the auto exposure control with high-speed communication.

However, there is room for improvement in reducing the delay of the AEC signal in the above-mentioned technique.

SUMMARY OF THE DISCLOSURE

Therefore, one of objects of an embodiment of the present disclosure is to provide a radiation imaging system capable of reducing the risk of transmission delay of the AEC signal and reducing the risk of invalid exposure.

An X-ray imaging system according to an embodiment of the present disclosure comprises a control apparatus that controls a radiation generating apparatus which exposes a radiation, and a radiation imaging apparatus that detects the exposed radiation and generates a radiation image, wherein the radiation imaging apparatus has a first communication mode in which a signal related to a stop of exposure of the radiation is wirelessly transmitted and a second communication mode in which at least one signal not related to the stop of exposure of the radiation is wirelessly transmitted, and wherein communication in the first communication mode includes communication at power lower than communication in the second communication mode.

Further features of the present disclosure will become apparent from the following description of exemplary embodiments with reference to the attached drawings.

BRIEF DESCRIPTION OF THE DRAWINGS

FIG. 3 is a schematic diagram for illustrating a sensor panel and an electrical component related to X-ray imaging according to the first embodiment.

FIG. 5 is a flowchart related to wireless communication of the X-ray imaging system according to the first embodiment.

FIG. 6 is a timing chart related to the wireless communication of the X-ray imaging system according to the first embodiment.

FIG. 9 is a schematic diagram for illustrating a sensor according to a third embodiment.

FIG. 10 is a flowchart related to wireless communication of an X-ray imaging system according to the third embodiment.

FIG. 11A is a timing chart related to the wireless communication of the X-ray imaging system according to the third embodiment.

FIG. 11B is a timing chart related to the wireless communication of the X-ray imaging system according to the third embodiment.

FIG. 11C is a timing chart related to the wireless communication of the X-ray imaging system according to the third embodiment.

DESCRIPTION OF THE EMBODIMENTS

Figure 1:
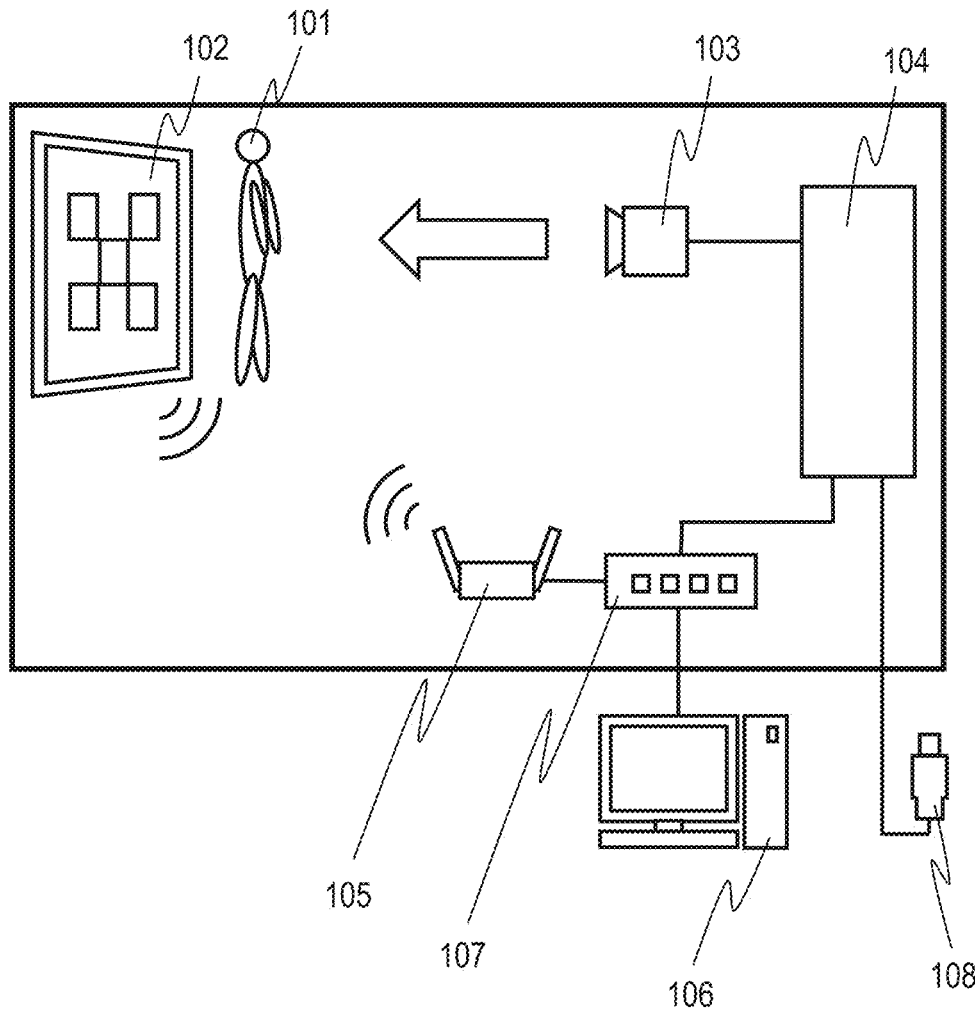
FIG. 1 is a schematic diagram for illustrating an X-ray imaging system according to a first embodiment.

According to a radiation imaging system of the present disclosure, it is possible to reduce the transmission delay of AEC signals caused by radio frequency interference. For example, in the technology described in the above-mentioned Japanese Patent No. 05914503, there is a probability which causes the radio frequency interference and a transmission delay if there is another wireless apparatus in the vicinity of the apparatus which performs wireless communication. This is because the risk of transmission delay due to the radio frequency interference may increase when the wireless communication is performed at a high output (high power) and wireless communication at a high speed generally results in the wireless communication at a high output, and therefore the risk of transmission delay due to the radio frequency interference may increase if the exposure stop signal is wirelessly communicated at the high output through the high-speed communication or the like. On the other hand, one embodiment of the present disclosure can provide a radiation imaging system capable of reducing the risk of transmission delay due to the radio frequency interference and reducing the risk of invalid exposure. Hereinafter, an embodiment of the present disclosure will be described based on a specific structure.

Preferred embodiments of the present disclosure will now be described in detail in accordance with the accompanying drawings. However, the dimensions, materials, shapes, relative positions of components, and the like described in the following embodiments can be freely set and may be modified depending on the configuration of an apparatus to which the present disclosure is applied or various conditions. In the drawings, the same reference numerals are used between drawings to indicate elements that are identical or functionally similar. In addition, parts of components, members, and processes that are not descriptively important in each drawing may be omitted.

In the following, a radiation imaging system using X-ray as an example of radiation will be described. However, the radiation may be X-ray or other radiation. In the following embodiments, the term radiation may include, for example, electromagnetic radiation such as X-rays and γ-rays, and particle radiation such as α-rays, β-rays, particle rays, proton rays, heavy ion rays, and meson rays.

First Embodiment

Hereinafter, an X-ray imaging system functioning as an example of a radiation imaging system according to a first embodiment of the present disclosure, which applied to a medical image diagnosis apparatus and the like, and an operation method thereof will be described with reference to FIG. 1 to FIG. 6. FIG. 1 is a schematic diagram for illustrating the X-ray imaging system according to the first embodiment.

The X-ray imaging system according to the first embodiment includes a sensor 102, an X-ray source 103, an exposure controlling apparatus 104, an AP (access point) 105, a PC (personal computer) 106, and an IF (interface) unit 107. The sensor 102 functions as an example of an X-ray imaging apparatus that detects X-rays transmitted through a subject 101 and generates an X-ray image based on the detected X-rays. The X-ray source 103 includes, for example, an X-ray tube, etc., and functions as an example of a radiation irradiating apparatus that irradiates the radiation under control by the exposure controlling apparatus 104. The exposure controlling apparatus 104 can control the operation of the X-ray source 103 by supplying a high voltage current to the X-ray source 103, and can control the start and stop of the X-ray irradiation by the X-ray source 103.

The AP 105 can transmit and receive data with wireless communication, and can also transmit and receive data with wired communication. The PC 106 can perform image processing of the obtained image, display the image, and input imaging information. The IF unit 107 can exchange information between devices such as the AP 105 and the PC 106, and transmit information indicating the start of exposure and information indicating the stop of exposure to the exposure controlling apparatus 104.

An exposure switch 108 is connected to the exposure controlling apparatus 104. When the subject 101 is in a predetermined position and in a predetermined posture, an operator such as a laboratory technician operates the exposure switch 108, so that a signal indicating the start of X-ray irradiation is transmitted to the exposure controlling apparatus 104 and the start of X-ray irradiation can be instructed. The input method of the signal indicating the start of X-ray irradiation is not limited to the operation of the exposure switch 108, but may be a method according to a desired configuration, such as the operation of the PC 106 or the operation of a tablet terminal (not shown).

Figure 2A:
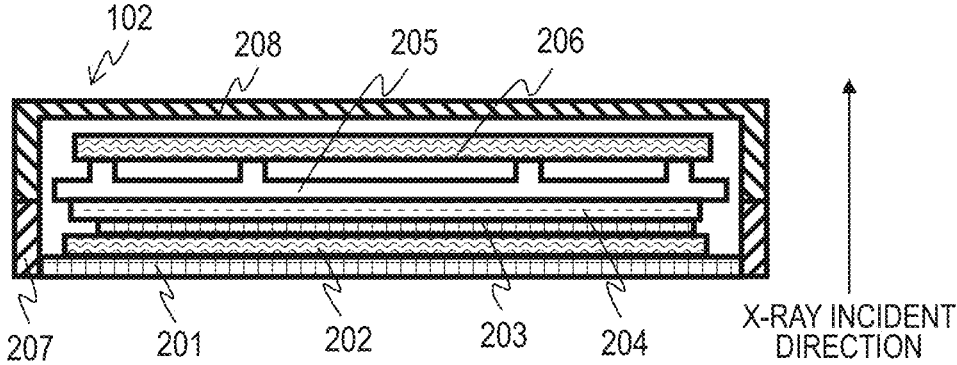
FIG. 2A is a schematic diagram for illustrating a sensor according to the first embodiment.

Next, the sensor 102 of the X-ray imaging system according to the first embodiment will be described with reference to FIG. 2A and FIG. 2B. FIG. 2A is a schematic diagram for illustrating the cross section of the sensor 102 according to the first embodiment. In FIG. 2A, the direction of incidence of X-rays is indicated by arrows.

The sensor 102 includes, from the X-ray incident surface side, an incident surface plate 201 made of a material such as CFRP (carbon fiber composite material), which has high X-ray transmissibility and high rigidity, and an impact absorbing member 202 formed of a foam or the like, which makes it difficult to transmit an impact from the X-ray incident surface side to the inside.

Next to the impact absorbing member 202, the sensor 102 includes a sensor panel 204 to which a scintillator 203 is attached. The scintillator 203 may include, for example, CsI or GOS, which converts the incident X-rays into visible light. The sensor panel 204 detects the light emitted by the scintillator 203 and generates an electrical signal for forming a two-dimensional image.

The sensor panel 204 is attached to a support base 205 formed of a steel material such as, for example, a magnesium alloy, an aluminum alloy, and a stainless steel, or a rigid material such as CFRP with an adhesive (not shown). Further, various electric substrates 206 for driving the sensor panel 204 to image an electric signal for forming a two-dimensional image and converting the electric signal into two-dimensional image data are attached to the support base 205. The various electric substrates 206 can be connected to the sensor panel 204 by an FFC (Flexible Flat Cable) or the like (not shown).

Further, in the sensor 102, the above-mentioned various components are covered with a front housing 207 bonded to the incident surface plate 201 by an adhesive or the like (not shown), and a rear housing 208 removably fastened to the front housing 207 by screws or the like (not shown).

Figure 2B:
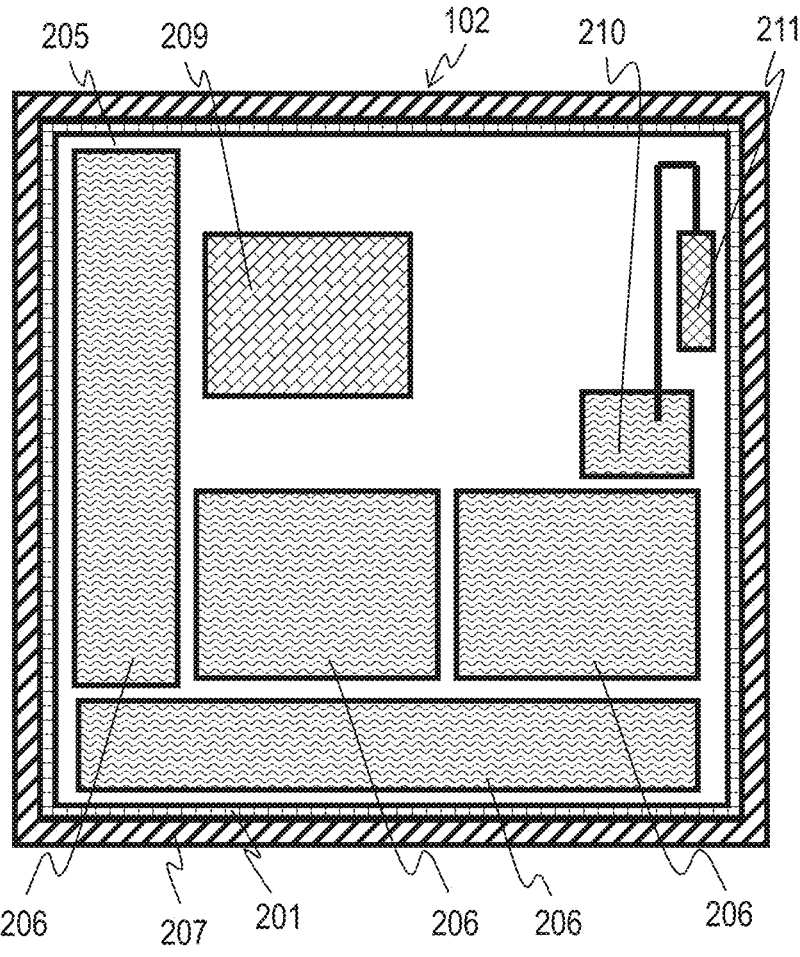
FIG. 2B is a schematic diagram for illustrating a sensor according to the first embodiment.

FIG. 2B is a schematic diagram for illustrating the sensor 102 viewed from the side opposite to the X-ray incident surface without the rear housing 208. As described above, on the rear side of the sensor 102 shown in FIG. 2B, the various electric substrates 206 for functioning the sensor 102 are disposed and a battery 209 for supplying power to the various electric substrates 206 and the sensor panel 204 is also disposed detachably.

Further, inside the sensor 102, a wireless module 210 for converting captured image data and various information into signals for the wireless communication, and an antenna 211 for transmitting the signals for the wireless communication to the outside are provided. Here, the wireless module 210 and the antenna 211 can perform wireless LAN communication in 2.4 GHz band and 5 GHz band.

In the rear housing 208, there is an opening in the vicinity of the antenna 211, and a dielectric component such as resin (not shown) is attached so as to cover the opening. Since the radio wave can transmit through the part covered by the dielectric component, the sensor 102 can perform the wireless communication with the outside through the part. With the above configuration, the sensor 102 can communicate with the AP 105 by the wireless communication. Therefore, the sensor 102 can communicate with the PC 106 through the AP 105 and the IF unit 107, image data, information related to imaging and the like, and can transmit a signal related to the stop of exposure to the exposure controlling apparatus 104.

Figure 3:
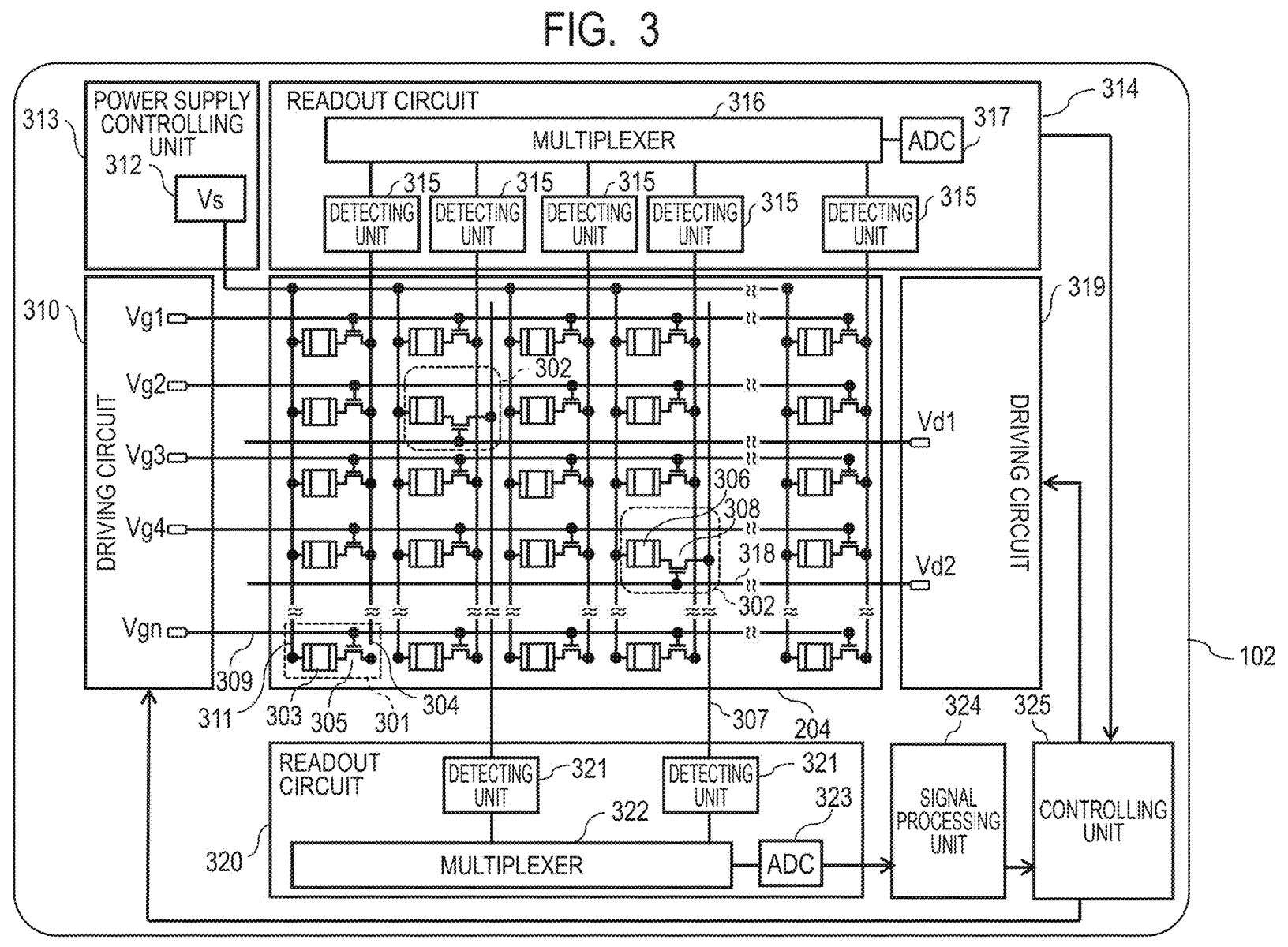

Next, a mechanism of driving the sensor 102 in the X-ray imaging system according to the first embodiment will be described with reference to FIG. 3. FIG. 3 is a schematic diagram for illustrating the sensor panel 204 and electrical components included in the sensor 102 according to the first embodiment. The sensor panel 204 includes a plurality of pixels for obtaining X-ray image data, which are arranged to constitute a plurality of rows and a plurality of columns.

In the following description, an area where the plurality of pixels are arranged in the sensor panel 204 is described as an imaging area. The plurality of pixels include a plurality of imaging pixels 301 for obtaining the X-ray image and a detecting pixel 302 for monitoring the irradiation of X-rays. The detecting pixel 302 is used as a detecting unit for performing the exposure control during the X-ray irradiation. That is, in the first embodiment, the detecting unit for performing the exposure control is arranged in the imaging area.

The imaging pixel 301 includes a conversion element 303 for converting the X-ray into an electrical signal, and a switch 305 arranged between a column signal line 304 and the conversion element 303. The detecting pixel 302 includes a conversion element 306 for converting the X-ray into an electrical signal, and a switch 308 arranged between a detecting signal line 307 and the conversion element 306. The detecting pixel 302 is arranged in the same column as a part of the plurality of imaging pixels 301.

In the first embodiment, the conversion element 303 and the conversion element 306 include a photoelectric conversion element that converts light converted from the X-ray by the scintillator 203 into an electrical signal.

The switch 305 and the switch 308 include a thin film transistor (TFT) of which an active region includes, for example, a semiconductor such as amorphous silicon or polycrystalline silicon. In the first embodiment, the polycrystalline silicon may be used as the active region.

The sensor 102 includes a plurality of column signal lines 304 and a plurality of driving lines 309. Each column signal line 304 corresponds to one column among a plurality of column in the imaging area. Each driving line 309 corresponds to one row among a plurality of row in the imaging are. The driving line 309 is driven by a driving circuit 310.

One of the two electrodes of the conversion element 303 is connected to one of main electrodes of the switch 305, and the other of the two electrodes of the conversion element 303 is connected to a bias line 311. Here, the bias line 311 extends along the column direction and is commonly connected to the electrodes of the plurality of conversion elements 303 arranged in the column direction. A bias voltage Vs is supplied to the bias line 311 from an element power supply circuit 312. A power supply controlling unit 313 includes a DC/DC converter (not shown), the element power supply circuit 312, and so on. The power supply controlling unit 313 receives voltage supplied from the battery 209 and generates an analog circuit power supply and a digital circuit power supply for performing drive control, the wireless communication, and the like.

The other main electrode of the switch 305 of the plurality of imaging pixels 301 constituting one column is connected to the column signal line 304. The control electrode of the switch 305 of the plurality of imaging pixels 301 constituting one row is connected to the common driving line 309. The plurality of column signal lines 304 are connected to a readout circuit 314. The readout circuit 314 includes a detecting unit 315, a multiplexer 316, and an analog-to-digital converter (AD converter) 317.

Each of the plurality of column signal lines 304 is connected to a corresponding detecting unit 315 of the plurality of detecting units 315 arranged in the readout circuit 314. One column signal line 304 corresponds to one detecting unit 315. The detecting unit 315 includes, for example, a differential amplifier. The multiplexer 316 selects a plurality of detecting units 315 in a predetermined order and supplies a signal from the selected detecting unit 315 to the AD converter 317. The AD converter 317 converts the supplied signal into a digital signal and outputs it.

One of the two electrodes of the conversion element 306 is connected to one of main electrodes of the switch 308, and the other of the two electrodes of the conversion element 306 is connected to the bias line 311. The other of the main electrodes of the switch 308 is connected to the detecting signal line 307. The control electrode of the switch 308 is connected to the driving line 318.

The sensor 102 may have one detecting signal line 307 or, as shown in FIG. 3, a plurality of detecting signal lines 307. One or a plurality of detecting pixels 302 are connected to one detecting signal line 307. The driving line 318 is driven by the driving circuit 319. One or more detecting pixels 302 are connected to one driving line 318. The detecting signal line 307 is connected to a readout circuit 320. The readout circuit 320 includes a detecting unit 321, a multiplexer 322, and an AD converter 323.

Each of the plurality of detecting signal lines 307 is connected to a corresponding detecting unit 321 of the plurality of detecting unit 321 in the readout circuit 320. One detecting signal line 307 corresponds to one detecting unit 321. The detecting unit 321 includes, for example, a differential amplifier. The multiplexer 322 selects a plurality of detecting unit 321 in a predetermined order and supplies a signal from the selected detecting unit 321 to the AD converter 323. The AD converter 323 converts the supplied signal into a digital signal and outputs it.

The output of the readout circuit 320 (AD converter 323) is supplied to a signal processing unit 324 and processed by the signal processing unit 324. The signal processing unit 324 outputs information indicating the irradiation of X-rays to the sensor 102 based on the output of the readout circuit 320 (AD converter 323). Specifically, the signal processing unit 324 can, for example, detect the irradiation of X-rays incident on the sensor 102 and calculate the irradiation amount and/or the accumulated irradiation amount of X-rays. The calculated irradiation amount and/or accumulated irradiation amount of X-rays can be used for the exposure control.

The controlling unit 325 can control each component of sensor 102, such as the driving circuit 310, 319 and the readout circuit 314, 320 based on information output from the signal processing unit 324 and control commands output from the PC 106.

In FIG. 3, for illustrative purposes, the power supply controlling unit 313, the driving circuit 310, 319, the readout circuit 314, 320, the signal processing unit 324, and the controlling unit 325 are represented on the same plane as the sensor panel 204. In contrast, each of these components may be present on the electrical substrate 206 shown in FIG. 2B.

For the sake of explanation, the detecting pixels 302 for dose detection and the imaging pixels 301 for image data generation are described as different, but they may be the same. That is, the conversion element 306 may be the same as the conversion element 303, the switch 308 may be the same as the switch 305, the detecting signal line 307 may be the same as the column signal line 304, and the driving line 318 may be the same as the driving line 309. Further, the readout circuit 320 and the readout circuit 314 may be common, and the driving circuit 319 and the driving circuit 310 may be common.

Next, the operation of the AEC of the X-ray imaging system using the sensor 102 will be described. In the AEC, X-rays incident on the X-ray detecting area of the sensor 102 are detected, and the accumulated irradiation amount, which is the accumulated value of dose (arrived dose) of the detected X-rays, is calculated, and it is determined whether the accumulated irradiation amount reaches the appropriate dose calculated from imaging-condition, etc. If it is determined that the accumulated irradiation amount reaches the appropriate dose, an exposure stop signal is transmitted to the exposure controlling apparatus 104 via the wireless communication, and the irradiation of X-rays by the X-ray source 103 is stopped based on the exposure stop signal. In a case where the AEC is performed by the mechanism described above, the delay of the wireless communication interferes with appropriate exposure control, and increases the risk of not obtaining the desired image and the risk of invalid exposure.

Figure 4:
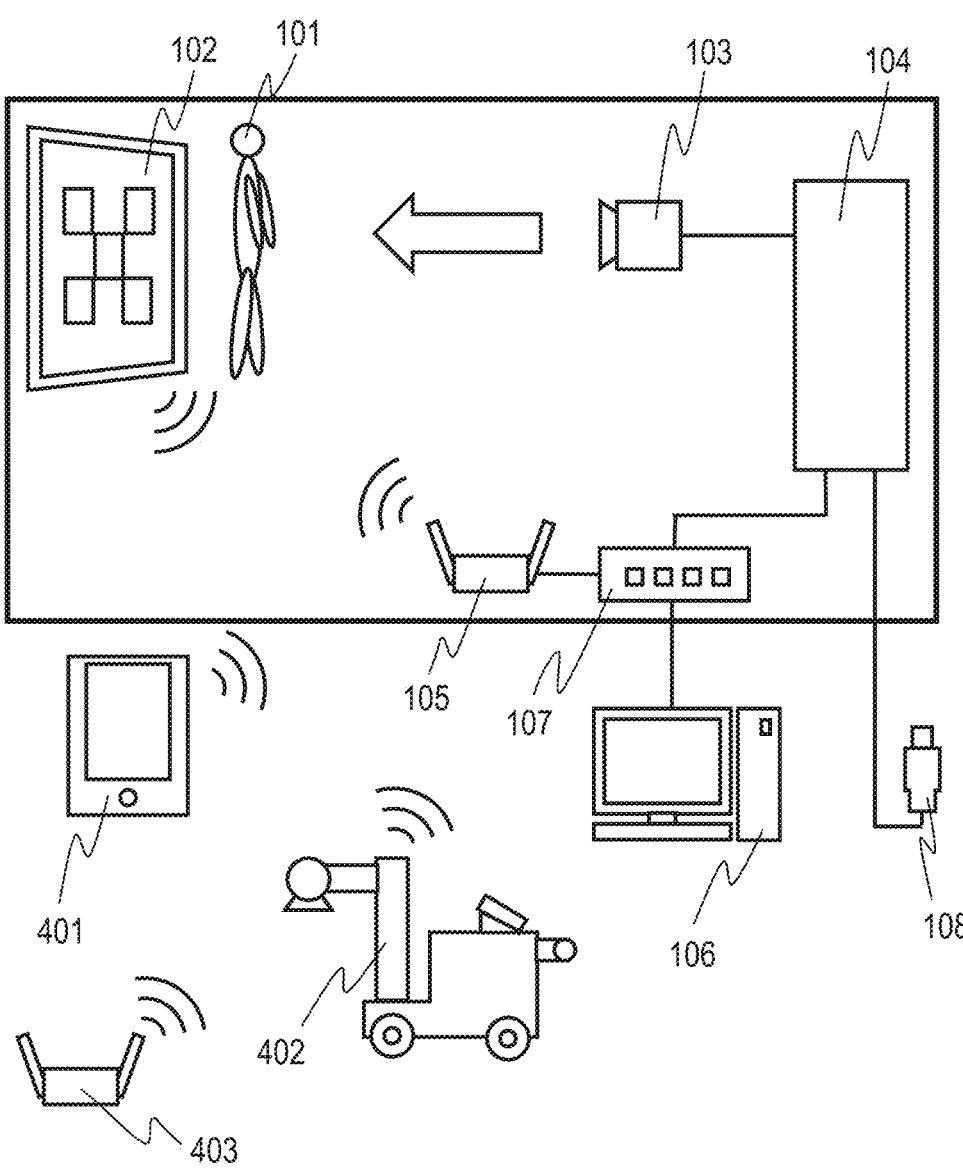
FIG. 4 is a schematic diagram for illustrating an X-ray imaging system related to a communication delay risk.

Next, a mechanism for reducing the communication delay risk according to the first embodiment will be described with reference to FIG. 4. The minimum configuration for X-ray imaging has been described in FIG. 1. However, in general, a hospital with an X-ray imaging system has many other wireless apparatuses. For example, as shown in FIG. 4, there may be a terminal 401 such as a tablet used by a physician or a nurse, a circuit car 402 used for a patient who cannot go to the X-ray imaging room, and a separate access point 403 outside the X-ray imaging room for communicating with them.

As described above, the wireless module 210 and the antenna 211 in the sensor 102 according to the first embodiment can perform the wireless LAN communication in the 5 GHz band and the wireless LAN communication in the 2.4 GHz band with peripheral apparatuses. Generally, in wireless communication, the higher the output (power), the lower the loss of communication and the higher the speed of communication. Therefore, in communication with a large amount of data, wireless communication at a high output may be desired. In contrast, in communication by wireless LAN, the Carrier Sense is performed to check whether other apparatuses are communicating in the same frequency band (channel) before communication. If other apparatuses are using the same channel, the wireless apparatus needs to wait for data transmission. Therefore, if a large number of wireless apparatuses are using the same channel in the proximity space, it is easy to cause waiting for data transmission and to cause delays in wireless communication.

On the other hand, if the wireless apparatus performs the wireless communication at a low output, the Carrier Sense may not be necessary. Therefore, the risk of transmission delay can be reduced by performing wireless communication at the low output.

Next, the wireless communication according to the first embodiment will be described with reference to FIG. 5 and FIG. 6. FIG. 5 is a flowchart for illustrating a series of processes according to the first embodiment. FIG. 6 is a timing chart related to the wireless communication of the X-ray imaging system according to the first embodiment. In the graph shown in FIG. 6, the horizontal axis represents the time lapse and the vertical axis represents the wireless communication output. Further, the diamond pattern portion represents the communication in the 5 GHz band and the grid pattern portion represents the communication in the 2.4 GHz band.

First, the operator inputs to the PC 106 imaging information related to imaging-condition, such as a dose, a maximum irradiation time, a tube current, a tube voltage, an X-ray detecting area (ROI) which is an area where X-rays should be monitored, and site information. The PC 106 transmits the input imaging information to the sensor 102 and the exposure controlling apparatus 104 in step S501. At this time, as shown in FIG. 6, the sensor 102 performs high-speed communication in a second communication mode in which a signal is transmitted at a high output PH in the 2.4 GHz band.

Next, in step S502, when the exposure switch 108 is depressed by the operator who determines that the imaging preparation is completed, the X-ray source 103 irradiate the X-rays according to the control by the exposure controlling apparatus 104. The irradiated X-rays pass through the subject 101 and enter the sensor 102.

In step S503, the sensor 102 detects X-rays incident on the X-ray detecting area (ROI) by the detecting pixel 302, and calculates the accumulated irradiation amount which is the accumulated value of the detected dose (arrived dose) by the signal processing unit 324. The controlling unit 325 calculates an appropriate dose from the site information, the imaging-condition, etc. input by the operator. Based on the information indicating the accumulated irradiation amount output from the signal processing unit 324, the controlling unit 325 determines whether the accumulated irradiation amount (detected dose) reaches the appropriate dose, which is a threshold value. For example, the controlling unit 325 determines whether the accumulated irradiation amount becomes the same as or larger than the appropriate dose.

In step S503, if it is determined by the controlling unit 325 that the accumulated irradiation amount reaches the appropriate dose, which is the threshold value, the process proceeds to step S504. On the other hand, if it is determined that the accumulated irradiation amount does not reach the appropriate dose, the process in step S503 is repeated.

In step S504, the controlling unit 325 generates an exposure stop signal indicating the timing to stop the X-ray irradiation. The controlling unit 325 may determine the timing to stop the X-ray irradiation based on the accumulated irradiation amount and the appropriate dose. The sensor 102 transmits the exposure stop signal to the exposure controlling apparatus 104 via the wireless module 210 and the antenna 211, and notifies the stop of the X-ray irradiation. At this time, the controlling unit 325 causes the wireless module 210 to generate the exposure stop signal at a low output PL with a low delay risk. If the wireless module 210 generates the exposure stop signal, the sensor 102 transmits the exposure stop signal via the antenna 211 in the first communication in which a signal is transmitted at the low output PL in the 2.4 GHz band. The exposure controlling apparatus 104 stops the irradiation of X-rays from the X-ray source 103 based on the transmitted exposure stop signal.

Thereafter, in step S505, the sensor 102 transmits the obtained X-ray image based on the X-rays transmitted through the subject 101 to the PC 106. Since the amount of data in the acquired image is large, the sensor 102 transmits the image data in the second communication mode in which signal communication is performed at the high output PH in the 2.4 GHz band, as shown in FIG. 6, and performs high-speed communication.

As described above, the X-ray imaging system according to the first embodiment can function as an example of a radiation imaging system which is capable of controlling the radiation imaging by the auto exposure control (AEC). The X-ray imaging system according to the first embodiment includes the X-ray source 103, the exposure controlling apparatus 104, and the sensor 102. The X-ray source 103 may function as an example of a radiation generating apparatus that exposes a radiation. The exposure controlling apparatus 104 may function as an example of a controller that controls the radiation generating apparatus. The sensor 102 may function as an example of a radiation imaging apparatus that detects the exposed radiation and generates a radiation image. The sensor 102 has a first communication mode in which an exposure stop signal as a signal related to the stop of exposure of the radiation is wirelessly transmitted, and a second communication mode in which radiation image data or imaging information is wirelessly transmitted. That is, the radiation image data and the imaging information means signals that are not related to the stop of exposure of the radiation. Communication in the first communication mode includes communication at power lower than communication in the second communication mode.

With this configuration, the X-ray imaging system according to the first embodiment can transmit signals related to the stop of exposure at low output. Therefore, since the retransmission of signal based on the influence of radio waves from other apparatuses is difficult to occur, the risk of communication delay can be reduced even if the AEC imaging is performed wirelessly, the risk of not obtaining a desired image can be reduced, and the risk of invalid exposure can be reduced.

Further, the sensor 102 includes the controlling unit 325 that can function as an example of a determining unit that determines whether the detected dose of radiation reaches a threshold. In this case, the controlling unit 325 determines whether the accumulated irradiation amount, which is detected dose of radiation, reaches an appropriate dose, which is a threshold, and the sensor 102 transmits the exposure stop signal to the exposure controlling apparatus 104. Therefore, since the sensor 102 only needs to transmit the exposure stop signal as the signal related to the stop of exposure, the signal related to the stop of exposure can be transmitted in a small volume, the increase in the transmission amount of the signal related to the stop of exposure can be suppressed, and the processing load related to communication can be reduced.

In the first embodiment, the sensor 102 determines whether or not the detected dose of X-rays reaches the appropriate dose, which is a threshold value, and transmits the exposure stop signal as the signal related to the stop of exposure. However, the configuration for determining whether or not the dose of X-rays reaches the threshold value is not limited to this. For example, the sensor 102 may transmit an arrived dose for each predetermined time period as a detection result to the exposure controlling apparatus 104 in the first communication mode as a signal related to the stop of exposure, and the exposure controlling apparatus 104 may calculate the accumulated value of the arrived dose to determine whether or not the accumulated value reaches the appropriate dose. In this case, the determining unit for determining whether or not radiation dose detected by the sensor 102 reaches the threshold may be provided in the exposure controlling apparatus 104.

Note that the communication in the first communication mode and the second communication mode may be the same communication system, and may include communication according to IEEE802.11 standard, for example. The communication frequency band (the first communication frequency band) in the first communication mode may include a communication frequency band in the 2.4 GHz band.

In the first embodiment, the sensor 102 performs the communication in the 2.4 GHz band in the second communication mode, but may perform the communication in the 5 GHz band. Even in this case, since the signal related to the stop of exposure is transmitted in the first communication mode in which the signal communication is performed at a low output, the risk of communication delay can be reduced, the risk of not obtaining a desired image can be reduced, and the risk of invalid exposure can be reduced.

Second Embodiment

Figure 7:
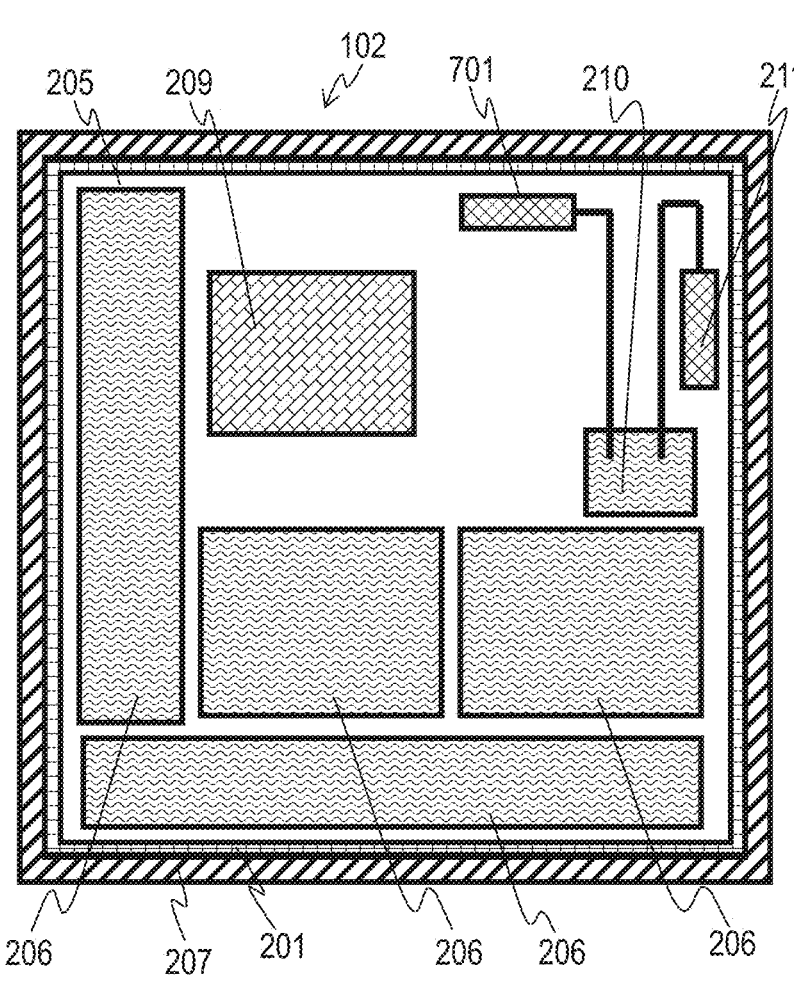
FIG. 7 is a schematic view for illustrating a sensor according to a second embodiment.

Next, a second embodiment of the present disclosure will be described with reference to FIG. 7 and FIG. 8. Since the configuration of the X-ray imaging system, the driving mechanism of the sensor, and the series of processing according to the second embodiment are the same as those of the first embodiment, the same reference numerals will be used to omit the description. First, the configuration of the sensor 102 of the X-ray imaging system according to the second embodiment will be described with reference to FIG. 7. Since the structure of cross section of the sensor 102 is equivalent to the structure of cross section of the sensor 102 according to the first embodiment shown in FIG. 2A, the description will be omitted. FIG. 7 is a schematic diagram for illustrating the sensor 102 when viewed from the side opposite to the X-ray incident surface without the rear housing 208.

The sensor 102 according to the second embodiment includes an antenna II 701, and not only the antenna 211 but also the antenna II 701 is connected to the wireless module 210. Both the antenna 211 and the antenna II 701 receive signals from the wireless module 210 and can communicate in the 2.4 GHz band and the 5 GHz band.

In the rear housing 208, there are openings in the vicinity of both the antenna 211 and the antenna II 701, and a dielectric component such as a resin (not shown) is attached so as to cover the openings. Since the radio wave can transmit through the part covered by the dielectric, the sensor 102 can perform the wireless communication with the outside through the part.

Next, with reference to FIG. 5 and FIG. 8, the difference between the wireless communication according to the second embodiment and the wireless communication according to the first embodiment will be described. FIG. 8 is a timing chart related to the wireless communication of the X-ray imaging system according to the second embodiment, and the communication of each antenna is shown for each time series. In the graph shown in FIG. 8, the horizontal axis represents the time lapse and the vertical axis represents the wireless communication output, and the diamond pattern portion represents communication in the 5 GHz band and the grid pattern portion represents communication in the 2.4 GHz band.

In step S501, as in the first embodiment, the PC 106 transmits imaging information including imaging-condition, such as dose, the maximum irradiation time, the tube current, the tube voltage, the X-ray detection area (ROI) which is the area where the X-rays should be monitored, and site information, to the sensor 102 and the exposure controlling apparatus 104. At this time, as shown in FIG. 8, the sensor 102 communicates via the antenna II 701 in the second communication mode in which a signal is transmitted at a high output PH in the 5 GHz band.

Since the processing in step S502 and step S503 is the same as the processing in step S502 and step S503 according to the first embodiment, the description thereof is omitted. In step S504, the controlling unit 325 causes the wireless module 210 to generate an exposure stop signal at a low output PL with a low delay risk in the 2.4 GHz band. If the wireless module 210 generates the exposure stop signal, the sensor 102, as shown in FIG. 8, transmits the exposure stop signal via the antenna 211 in the first communication mode in which a signal is transmitted at the low output PL in the 2.4 GHz band.

Figure 8:
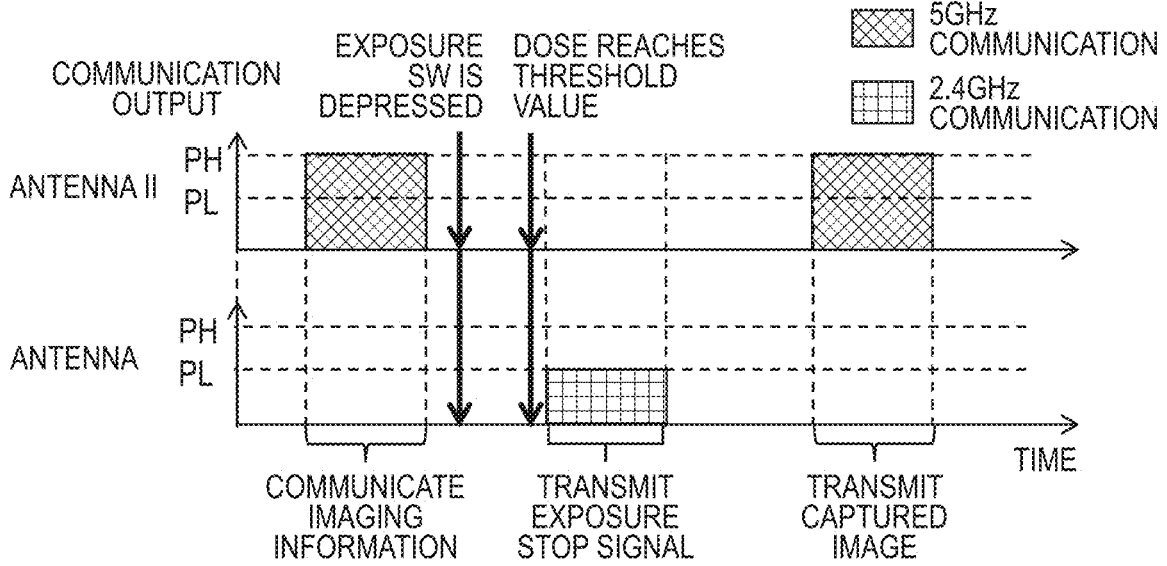
FIG. 8 is a timing chart related to wireless communication of an X-ray imaging system according to the second embodiment.

In step S505, since the volume of data of the obtained image is large, the sensor 102, as shown in FIG. 8, transmits image data via the antenna II 701 in the second communication mode in which a signal is transmitted at the high output PH in the 5 GHz band.

As described above, the sensor 102 according to the second embodiment has an antenna 211 that functions as an example of a first antenna and an antenna II 701 that functions as an example of a second antenna. Further, the sensor 102 communicates in the first communication mode using the antenna 211 and communicates in the second communication mode using the antenna II 701. Note that communication in the first communication mode may include communication in the first communication frequency band, and communication in the second communication mode may include communication in the second communication frequency band different from the first communication frequency band.

Even in this configuration, since the signal related to the stop of exposure is transmitted in the first communication mode in which the signal communication is performed at the low output, the risk of not obtaining the desired image can be reduced and the risk of invalid exposure can be reduced. Furthermore, by using a plurality of antennas, the frequency band and output used for each antenna can be separated, and communication other than the communication related to the stop of exposure in the AEC can be performed, for example, at a higher speed of the 5 GHz band.

In the second embodiment, the sensor 102 may also transmit an arrived dose for each predetermined time as a detection result to the exposure controlling apparatus 104 in the first communication mode as the signal related to the stop of exposure, and the exposure controlling apparatus 104 may calculate the accumulated value of the arrived dose and determine whether the accumulated value reaches the appropriate dose. In this case, the determining unit for determining whether the radiation dose detected by the sensor 102 reaches the threshold value may be provided in the exposure controlling apparatus 104.

Third Embodiment

Figure 9:
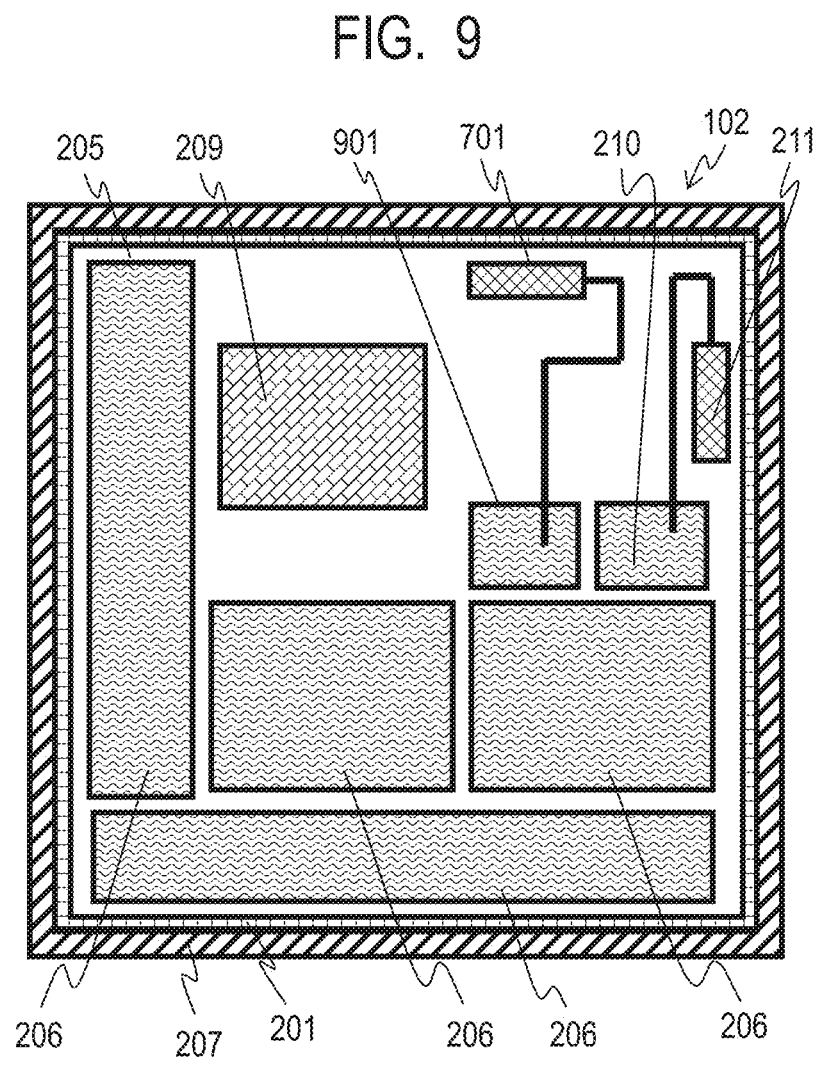

A third embodiment of the present disclosure will be described with reference to FIG. 9 to FIG. 11C. Since the configuration of the X-ray imaging system and the driving mechanism of the sensor are the same as those of the first embodiment, the description will be omitted using the same reference numerals. First, the configuration of the sensor 102 of the X-ray imaging system according to the third embodiment will be described with reference to FIG. 9. Since the structure of cross section of the sensor 102 is equivalent to the structure of cross section of the sensor 102 of the first embodiment shown in FIG. 2A, description will be omitted. FIG. 9 is a schematic diagram for illustrating the sensor 102 when viewed from the side opposite to the X-ray incident surface without the rear housing 208.

In the third embodiment, the antenna 211 is connected to the wireless module 210. The sensor 102 includes the wireless module II 901 and the antenna II 701, and the antenna II 701 is connected to the wireless module II 901. Since the antenna 211 and the antenna II 701 receive signals from different wireless modules, it is not necessary to switch the frequency band and the output in the wireless module, and communication with a plurality of outputs can be performed simultaneously.

As in the second embodiment, each of the rear housing 208 has an opening in the vicinity of both the antenna 211 and the antenna II 701, and a dielectric component, such as resin (not shown), is attached so as to cover the opening. Since the radio wave can transmit through the part covered by the dielectric, the sensor 102 can perform the wireless communication with the outside through the part.

Next, the wireless communication of the third embodiment will be described with reference to FIG. 10 to FIG. 11C. FIG. 10 is a flowchart for illustrating a series of processes according to the third embodiment. FIG. 11A to FIG. 11C are timing charts related to the wireless communication of the X-ray imaging system according to the third embodiment, and show the wireless communication using each antenna for each time series. In the graphs shown in FIG. 11A to FIG. 11C, the horizontal axis represents time lapse and the vertical axis represents the wireless communication output, and the diamond pattern portion represents communication in the 5 GHz band and the grid pattern portion represents communication in the 2.4 GHz band.

In step S501, the PC 106 transmits, as in the first embodiment, imaging information including imaging-condition, such as dose, maximum irradiation time, tube current, tube voltage, X-ray detection area (ROI) which is the area where X-rays should be monitored, and site information, to the sensor 102 and the exposure controlling apparatus 104. At this time, as shown in FIG. 11A, the sensor 102 performs signal communication via the antenna II 701 in a second communication mode in which a signal is transmitted at a high output PH in the 5 GHz band.

Since the processing in steps S502 and S503 is the same as the processing in steps S502 and S503 according to the first embodiment, description thereof will be omitted. In step S503, if it is determined by the controlling unit 325 that the accumulated irradiation amount reaches the appropriate dose, which is the threshold value, the process proceeds to step S1004.

In step S1004, as shown in FIG. 11A, the sensor 102 transmits an exposure stop signal in the first communication mode in which a signal at a low output PL in the 2.4 GHz band and a signal at the high output PH in the 5 GHz band are transmitted. Specifically, the controlling unit 325 first causes the wireless module 210 to generate the exposure stop signal at the low output PL with a low delay risk in the 2.4 GHz band. If the wireless module 210 generates the exposure stop signal, the sensor 102 transmits the exposure stop signal via the antenna 211 at the low output PL in the 2.4 GHz band. If the communication via the antenna 211 is completed, the controlling unit 325 causes the wireless module II 901 to generate the exposure stop signal at the high output PH in the 5 GHz band. If the wireless module II 901 generates the exposure stop signal, the sensor 102 transmits the exposure stop signal via the antenna II 701 at the high output PH in the 5 GHz band.

In step S505, since the volume of data of the obtained image is large, the sensor 102 transmits the image data via the antenna II 701 in the second communication mode in which signal communication is performed at the high output PH in the 5 GHz band, as shown in FIG. 11A.

As described above, the sensor 102 according to the third embodiment can perform the communication in the first communication mode using the antenna 211 and the antenna II 701. In this case, the communication in the first communication mode can include the communication using the antenna 211 at power lower than that in the second communication mode and communication using the antenna II 701 at power equivalent to that in the second communication mode. More specifically, the sensor 102 can communicate in the first communication mode at power lower than that in the second communication mode and then at power equivalent to that in the second communication mode.

Even in this configuration, since the signal related to the stop of exposure is transmitted in the first communication mode for signal communication at the low output, the risk of not obtaining the desired image can be reduced and the risk of invalid exposure can be reduced. Furthermore, since the exposure stop signal can be transmitted without interruption by signal transmission at the low output and signal transmission at the high output, the risk of not obtaining the desired image can be reduced and the risk of invalid exposure can be reduced even in a case where an error occurs in the signal transmission at the low output. In addition, by using a plurality of antennas, the frequency band and output used for each antenna can be separated, and communication other than the communication related to the stop of exposure in the AEC can be performed at a higher speed of 5 GHz band.

In the third embodiment, the controlling unit 325 generates and transmits the exposure stop signal at the high output PH in the 5 GHz band via the wireless module II 901 and the antenna II 701 after the communication using the antenna 211 is finished. In contrast, the controlling unit 325 may simultaneously generate the stop signal transmitted from the wireless module 210 and the stop signal transmitted from the wireless module II 901. In this case, the stop signal is transmitted through the wireless module 210 and the antenna 211 first, and after confirming that the communication is finished, the stop signal can be transmitted through the wireless module II 901 and the antenna II 701.

In addition, the third embodiment presents an example in which the sensor 102 transmits the exposure stop signal at the high output PH without interruption after transmitting the exposure stop signal at the low output. In contrast, the sensor 102 may transmit the exposure stop signals at a timing such that the exposure stop signal at the low output PL overlaps the exposure stop signal at the high output PH in the first communication mode, as shown in FIG. 11B. In this case, the sensor 102 may alternate between the communication at power lower than that at the second communication mode and communication at power equivalent to that at the second communication mode, in the first communication mode. The same effect can be achieved in this configuration. In addition, the risk of interruption of the exposure stop signal can be reduced.

Further, the sensor 102 may transmit the exposure stop signal at the low output PL and the exposure stop signal at the high output PH at the same timing in the first communication mode, as shown in FIG. 11C. In this case, the sensor 102 may simultaneously communicate in the first communication mode at power lower than that in the second communication mode and at power equivalent to that in the second communication mode. The same effect as described above can also be achieved in this configuration. In addition, preferable performance of the communication in the 2.4 GHz band and the communication in the 5 GHz band can both be obtained, and the risk of communication delay can be further reduced, the risk of not obtaining the desired image can be reduced, and the risk of invalid exposure can be reduced.

In the third embodiment, the sensor 102 may transmit an arrived dose for each predetermined time as a result of detection to the exposure controlling apparatus 104 at the first communication mode as the signal related to the stop of exposure, and the exposure controlling apparatus 104 may calculate the accumulated value of the arrived dose and determine whether or not the accumulated value reaches the appropriate dose. In this case, the determining unit for determining whether or not the radiation dose detected by the sensor 102 reaches the threshold value may be provided in the exposure controlling apparatus 104.

In the first to third embodiments, the sensor 102, which functions as an example of the radiation imaging apparatus, is an indirect conversion type detector that converts a radiation into visible light by using a scintillator and converts the visible light into an electrical signal by using a photoelectric conversion element. In contrast, the radiation imaging apparatus may be a direct conversion type detector that directly converts an incident radiation into an electrical signal.

According to the first to third embodiments of the present disclosure, the risk of transmission delay due to the radio frequency interference can be reduced, and the risk of invalid exposure can be reduced.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The processor or circuit may include a central processing unit (CPU), a micro processing unit (MPU), a graphics processing unit (GPU), an application specific integrated circuit (ASIC), or a field programmable gateway (FPGA). The processor or circuit may also include a digital signal processor (DSP), a data flow processor (DFP), or a neural processing unit (NPU).

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2023-084385, filed May 23, 2023, which is hereby incorporated by reference herein in its entirety.

What is claimed is:
1. A radiation imaging system comprising:
a control apparatus configured to control a radiation generating apparatus arranged to expose a radiation; and a radiation imaging apparatus arranged to detect the exposed radiation and generate a radiation image, wherein:

the radiation imaging apparatus has a first communication mode in which a signal related to a stop of exposure of the radiation is wirelessly transmitted and a second communication mode in which at least one signal not related to the stop of exposure of the radiation is wirelessly transmitted;

communication in the first communication mode includes communication at power lower than communication in the second communication mode;

the radiation imaging apparatus includes a first antenna and a second antenna;

the radiation imaging apparatus is configured to perform the communication in the first communication mode using the first antenna; and the radiation imaging apparatus is configured to perform the communication in the second communication mode using the second antenna.

2. The radiation imaging system according to claim 1, wherein the radiation imaging apparatus is arranged to perform the communication in the first communication mode using the first antenna and the second antenna.

3. The radiation imaging system according to claim 2, wherein the communication in the first communication mode includes communication using the first antenna at power lower than that in the second communication mode and communication using the second antenna at power equivalent to that in the second communication mode.

4. The radiation imaging system according to claim 3, wherein the radiation imaging apparatus is configured to, in the first communication mode, perform the communication at the power equivalent to that in the second communication mode after performing the communication at the power lower than that in the second communication mode.

5. The radiation imaging system according to claim 3, wherein the radiation imaging apparatus is configured to, in the first communication mode, simultaneously perform the communication at the power lower than that in the second communication mode and the communication at the power equivalent to that in the second communication mode.

6. The radiation imaging system according to claim 3, wherein the radiation imaging apparatus is configured to, in the first communication mode, alternate between the communication at the power lower than that in the second communication mode and the communication at the power equivalent to that in the second communication mode.

7. The radiation imaging system according to claim 1, wherein:

the radiation imaging system is capable of controlling radiation imaging by auto exposure control; and the radiation imaging apparatus includes a determining unit configured to determine whether a dose of the detected radiation reaches a threshold.

8. The radiation imaging system according to claim 1, wherein:

the radiation imaging system is capable of controlling radiation imaging by auto exposure control; and the controlling apparatus includes a determining unit configured to determine whether a dose of the radiation detected by the radiation imaging apparatus reaches a threshold.

9. The radiation imaging system according to claim 1, wherein a communication system of the first communication mode communication is the same as a communication system of the second communication mode.

10. The radiation imaging system according to claim 9, wherein the communication system of the first communication mode includes communication in IEEE802.11 standard.

11. The radiation imaging system according to claim 1, wherein:

the communication in the first communication mode includes communication in a first communication frequency band, and the communication in the second communication mode includes communication in a second communication frequency band different from the first communication frequency band.

12. The radiation imaging system according to claim 11, wherein the first communication frequency band includes a communication frequency band in a 2.4 GHz band.

13. A method of operating a radiation imaging system comprising a controlling apparatus configured to control a radiation generating apparatus arranged to expose a radiation and a radiation imaging apparatus arranged to detect the exposed radiation and generate a radiation image, the method comprising:

wirelessly transmitting a signal related to a stop of exposure of the radiation in a first communication mode by the radiation imaging apparatus; and wirelessly transmitting at least one signal not related to the stop of exposure of the radiation in a second communication mode by the radiation imaging apparatus, wherein:

communication in the first communication mode includes communication at power lower than communication in the second communication mode;

the communication in the first communication mode is performed using a first antenna included in the radiation imaging apparatus by the radiation imaging apparatus; and the communication in the second communication mode is performed using a second antenna included in the radiation imaging apparatus by the radiation imaging apparatus.

14. A non-transitory computer-readable storage medium having stored thereon a program, for causing, when executed by a computer, the computer to execute a method of operating a radiation imaging system, the method comprising:

wirelessly transmitting a signal related to a stop of exposure of the radiation in a first communication mode by a radiation imaging apparatus; and wirelessly transmitting at least one signal not related to the stop of exposure of the radiation in a second communication mode by the radiation imaging apparatus, wherein:

communication in the first communication mode includes communication at power lower than communication in the second communication mode;

the communication in the first communication mode is performed using a first antenna included in the radiation imaging apparatus by the radiation imaging apparatus; and the communication in the second communication mode is performed using a second antenna included in the radiation imaging apparatus by the radiation imaging apparatus.

* * * * *